US011324547B2

(12) United States Patent
VanDusseldorp, Sr. et al.

(10) Patent No.: US 11,324,547 B2
(45) Date of Patent: May 10, 2022

(54) ELECTROSURGICAL PROBE AND KIT AND METHOD OF USING

(71) Applicant: endoMedical Concepts,Inc., Punta Gorda, FL (US)

(72) Inventors: Gregg Alan VanDusseldorp, Sr., Punta Gorda, FL (US); Keldon S. Pickering, Mt. Vernon, WA (US)

(73) Assignee: endoMedical Concepts, Inc., Punta Gorda, FL (US)

( * ) Notice: Subject to any disclaimer, the term of this patent is extended or adjusted under 35 U.S.C. 154(b) by 600 days.

(21) Appl. No.: 16/126,287

(22) Filed: Sep. 10, 2018

(65) Prior Publication Data

US 2019/0069947 A1 Mar. 7, 2019

Related U.S. Application Data

(62) Division of application No. 14/716,150, filed on May 19, 2015, now Pat. No. 10,070,917.

(60) Provisional application No. 62/000,262, filed on May 19, 2014.

(51) Int. Cl.
*A61B 18/14* (2006.01)
*A61B 17/00* (2006.01)
*A61B 18/00* (2006.01)

(52) U.S. Cl.
CPC ........ *A61B 18/149* (2013.01); *A61B 18/1482* (2013.01); *A61B 18/1485* (2013.01); *A61B 2017/0023* (2013.01); *A61B 2018/00011* (2013.01); *A61B 2018/00023* (2013.01); *A61B 2018/00196* (2013.01); *A61B 2018/00517* (2013.01); *A61B 2018/00559* (2013.01); *A61B 2018/1495* (2013.01); *A61B 2218/002* (2013.01)

(58) Field of Classification Search
CPC .............. A61B 18/149; A61B 18/1485; A61B 18/1482; A61B 2018/00011; A61B 2018/00023; A61B 2018/00196; A61B 2018/00517; A61B 2018/00559; A61B 2018/1495; A61B 2218/002; A61B 2017/0023
See application file for complete search history.

(56) References Cited

U.S. PATENT DOCUMENTS 6,106,521 A * 8/2000 Blewett .............. A61B 18/1477
600/105
2009/0065565 A1* 3/2009 Cao ........................ A61B 90/90
235/375

* cited by examiner

*Primary Examiner* — Tammie K Marlen
(74) *Attorney, Agent, or Firm* — Hartman Global IP Law; Gary M. Hartman; Domenica N.S. Hartman

(57) ABSTRACT

Electrosurgical probes for treating tissue, and surgical procedures that make use of such probes. Such a probe includes a working element having a core member, a sheath secured to the working element, and a conductor disposed in a first internal longitudinal channel of the core member and having an active electrode coupled thereto. The sheath has a passage in which the core member is disposed, and the passage has an opening at a distal end of the sheath. The conductor is reciprocable within the sheath and adapted to carry a radio frequency current to and from the active electrode, which extends from the opening at the distal end of the sheath. An irrigation channel is defined by a second internal longitudinal channel of the core member. The electrosurgical probe is marked as disposable and not for reuse in a medical procedure performed on more than one patient.

18 Claims, 3 Drawing Sheets

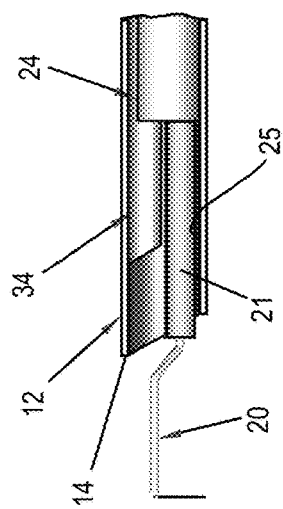
FIG. 3
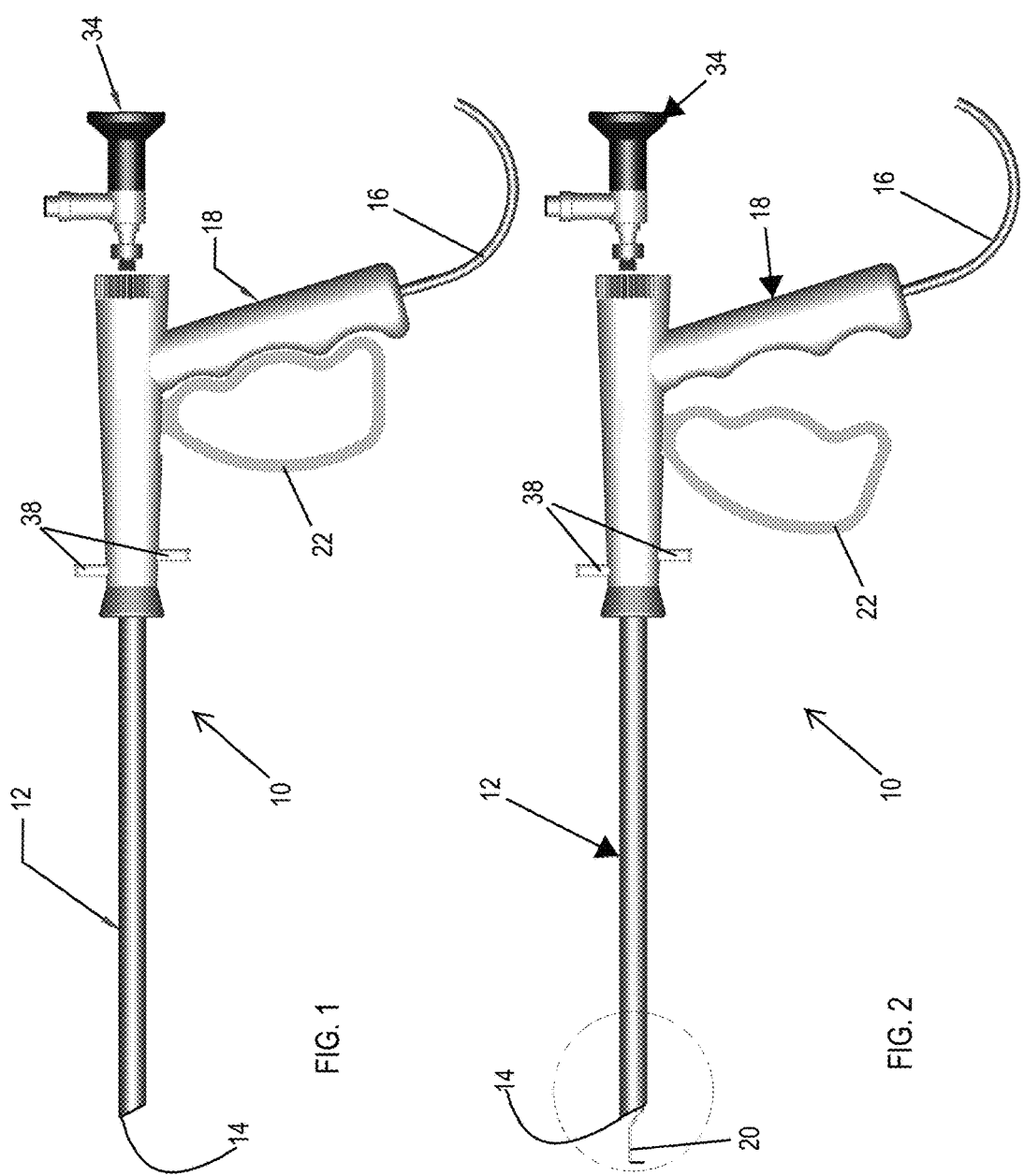
FIG. 1
FIG. 2

ELECTROSURGICAL PROBE AND KIT AND METHOD OF USING

CROSS REFERENCE TO RELATED APPLICATIONS

This is a division patent application of U.S. patent application Ser. No. 14/716,150, filed May 19, 2015, now U.S. Pat. No. 10,070,917, which claims the benefit of U.S. Provisional Application No. 62/000,262, filed May 19, 2014. The contents of these prior applications are incorporated herein by reference.

BACKGROUND OF THE INVENTION

The present invention relates to electrosurgical probes for treating damaged, diseased or enlarged tissue, and to surgical procedures that make use of such probes.

Electrosurgical effects can be accomplished by applying a highly damped radio frequency (RF) current to tissue through an electrode in the form of an active (+) electrode (tip) of an electrosurgical (electrocautery) probe, from which the RF current flows to a ground (−) electrode. RF electrosurgical probes (RF probes), such as those commonly used in urological and hysteroscopic procedures, are said to be monopolar or bipolar or said to have a monopolar or bipolar operating mode, depending on their electrode configuration. RF probes operating in a monopolar mode utilize a single (active) electrode (tip) and rely on external grounding of a patient (e.g., a ground electrode in the form of a patient plate) to cause current flow from the active electrode to tissue of the patient. RF probes operating in a bipolar mode have two electrodes, typically designated as active and return electrodes, and current flow is localized between these electrodes. As it passes through tissue from the active electrode to the ground or return electrode, the RF current resects (cuts), coagulates and/or ablates (desiccates) the tissue, depending on the type of probe and the RF power and wave length combinations used. RF electrosurgical probes are typically placed through a resectoscope (used in urological procedures), hysteroscope (used in gynecological procedures) or other device, which is often equipped with a telescope so that the active electrode of the probe is in direct view of the surgeon at all times. Irrigating solutions are commonly used as a distention medium and a coolant for the active electrodes of RF probes during electrosurgical procedures.

Resectoscopes and hysteroscopes (hereinafter referred to as electrosurgical probes) have been used for decades to diagnose and treat medical conditions in the human bladder and the uterus, respectively. Electrosurgical resection refers to procedures by which damaged, diseased or enlarged tissue is removed with an electrosurgical probe. A nonlimiting example is transurethral resection of the prostate (TURP), in which prostate tissue is removed by means of an active electrode (for example, a cutting loop) passed through the urethra by means of a resectoscope. This procedure has served as the historical treatment of benign prostate hypertrophy (BPH)), commonly known as "enlarged prostate," and prostatitus. Bladder tumors and cysts in men and women are also treated by electrosurgical resection. Electrosurgical ablation refers to procedures by which an electrosurgical probe is used to ablate (dessicate) tissue, which eventually sloughs off instead of being immediately removed on contact with the electrode. A nonlimiting example of an electrosurgical ablation procedure is endometrial ablation to treat endometriosis in women, in which tissue is removed by means of roller that serves as the active electrode. Another example is transurethral ablation of the prostate (TUAP), in which prostate tissue is ablated by means of an electrocautery probe passed over a stylet/obturator or guide wire, through the prostatic urethra.

In addition to its electrode, an electrosurgical probe typically includes a working element equipped with a power cord for connection to an RF electrosurgical current generator, and a sheath that extends from the working element and through which one or more conductors are routed to deliver RF current to the electrode protruding from a distal end of the sheath. The probe is also typically equipped with a telescope and/or light source disposed in one or more internal channels within the sheath to allow direct vision during placement and use of the probe. The electrode and its conductor(s) may be capable of reciprocal movement within the sheath through the operation of an actuation lever of the working element. The sheath may also define an internal flow channel to enable an irrigation fluid to be delivered for immersion cooling of the electrode. The RF generator, light source, and telescope are capital equipment and available in a typical surgical suite. While electrosurgical probe electrodes are disposable and therefore do not require sterilization after use, the remaining components of a electrosurgical probe, including the working element, sheath and telescope, are typically formed of stainless steels or another durable metallic material and durable heat-resistant plastics that enable these components to be reused following re-sterilization, for example, using an autoclave and/or ethylene oxide gas. As such, electrosurgical probes typically have high initial purchase costs. The distal end of the sheath is often equipped with a plastic tip that becomes damaged over time, in some cases after a single use, as a result of the high RF current levels, necessitating that the sheath undergo an expensive and time-consuming repair. Also due to the RF currents, metal components of an electrosurgical probe require electrical insulation to protect the surgeon from receiving shocks and burns during use of the probe. Even so, surgeons are commonly required to wear two pairs of latex gloves as a safety precaution.

Sterilization can be a complicated process, particularly in view of the internal channels within the sheath that accommodate a light source, telescope, and/or cooling flow stopcocks and channels. Furthermore, components of reusable electrosurgical probes are conventionally individually reprocessed, sterilized, and packaged, and then kept in drawers, cabinets, and carts accessible to the surgical team. If any of the components are unavailable or the wrong size, the procedure cannot go forward. Generally, hospitals have additional electrosurgical probes on hand in case one fails during surgery. However, at times when case loads are high, a physician may be forced to either wait for another unit to be sterilized or cancel the surgery.

ISO regulations require disposable (i.e., single-use) medical devices to be marked with the ② symbol to indicate that the devices are disposable and not for reuse in a medical procedure performed on more than one patient. Since the late 1980's, the use of disposable (sterile, one-time use) surgical instruments and devices has dramatically increased in the United States. This trend of cycling from reusable to disposable surgical instruments and devices is taking place now in countries around the world as their economies grow, as is the awareness of the risks and costs associated with hospital-acquired infections, especially those in the operating room. This trend is driven by numerous factors, such as sterility assurance, quality/performance, reducing cross contamination, and cost factors (cost control, convenience, and patient charges).

BRIEF DESCRIPTION OF THE INVENTION

The present invention provides electrosurgical probes for treating damaged, diseased or enlarged tissue, and to surgical procedures that make use of such probes.

According to one aspect of the invention, an electrosurgical probe is provided that includes a disposable working element comprising a core member having a plurality of internal longitudinal channels, a disposable elongate sheath secured to the working element, and a conductor disposed in a first of the internal longitudinal channels of the core member and having an active electrode coupled thereto. The sheath has a sheath passage in which the core member is disposed such that the sheath surrounds the core member, and the sheath passage has an opening at a distal end of the sheath. The conductor is reciprocable within the sheath and adapted to carry a radio frequency current to and from the active electrode. The active electrode extends from the opening at the distal end of the sheath and is configured to perform cutting, coagulation, or ablation of tissue when the radio frequency current flows to the active electrode. An irrigation channel is defined by a second of the internal longitudinal channels of the core member and configured to couple with an irrigation fluid source and provides an irrigation fluid to the active electrode from the irrigation fluid source. The working element further has means for reciprocating the active electrode relative to the sheath, and the sheath and the working element, including the core member and the reciprocating means thereof, are each single-use components formed of disposable materials and the electrosurgical probe is marked as disposable and not for reuse in a medical procedure performed on more than one patient.

According to another aspect of the invention, a method of using an electrosurgical probe to perform a medical procedure includes placing within a patient an active electrode of a electrosurgical probe that comprises a working element and an elongate sheath from which the active electrode protrudes, wherein the sheath and the working element are each single-use components formed of disposable materials and the electrosurgical probe is marked as disposable and not for reuse in a medical procedure performed on more than one patient. A single electrosurgical procedure is then performed on the patient using the active electrode of the electrosurgical probe, after which the working element, the sheath, and the active electrode are discarded, such that the placing and performing steps are the first and only medical procedure in which the working element, the sheath, and the active electrode are used.

A technical effect of the invention is that the disposable electrosurgical probe can be offered as a kit, in which the working element, sheath, core member, and one or more electrodes are all disposable components of the kit.

Other aspects and advantages of this invention will be better appreciated from the following detailed description.

BRIEF DESCRIPTION OF THE DRAWINGS

FIG. 1 is a side view representing an electrosurgical probe in accordance with a nonlimiting embodiment of this invention.

FIG. 2 represents an electrode protruding from a distal end of a sheath of the electrosurgical probe of FIG. 1 as a result of operating a handle of the working element.

FIG. 3 represents a partial cutaway view of the distal end of the sheath of FIG. 2, showing the electrode protruding therefrom and revealing an electrode connection and irrigation tube within the sheath.

DETAILED DESCRIPTION OF THE INVENTION

Figure 5:
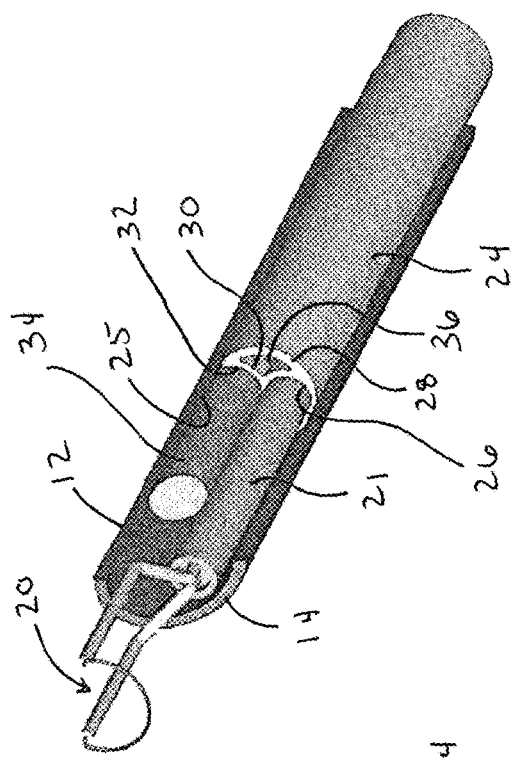
FIG. 5 represents a detailed perspective view of the partial cutaway view of FIG. 4.
Figure 4:
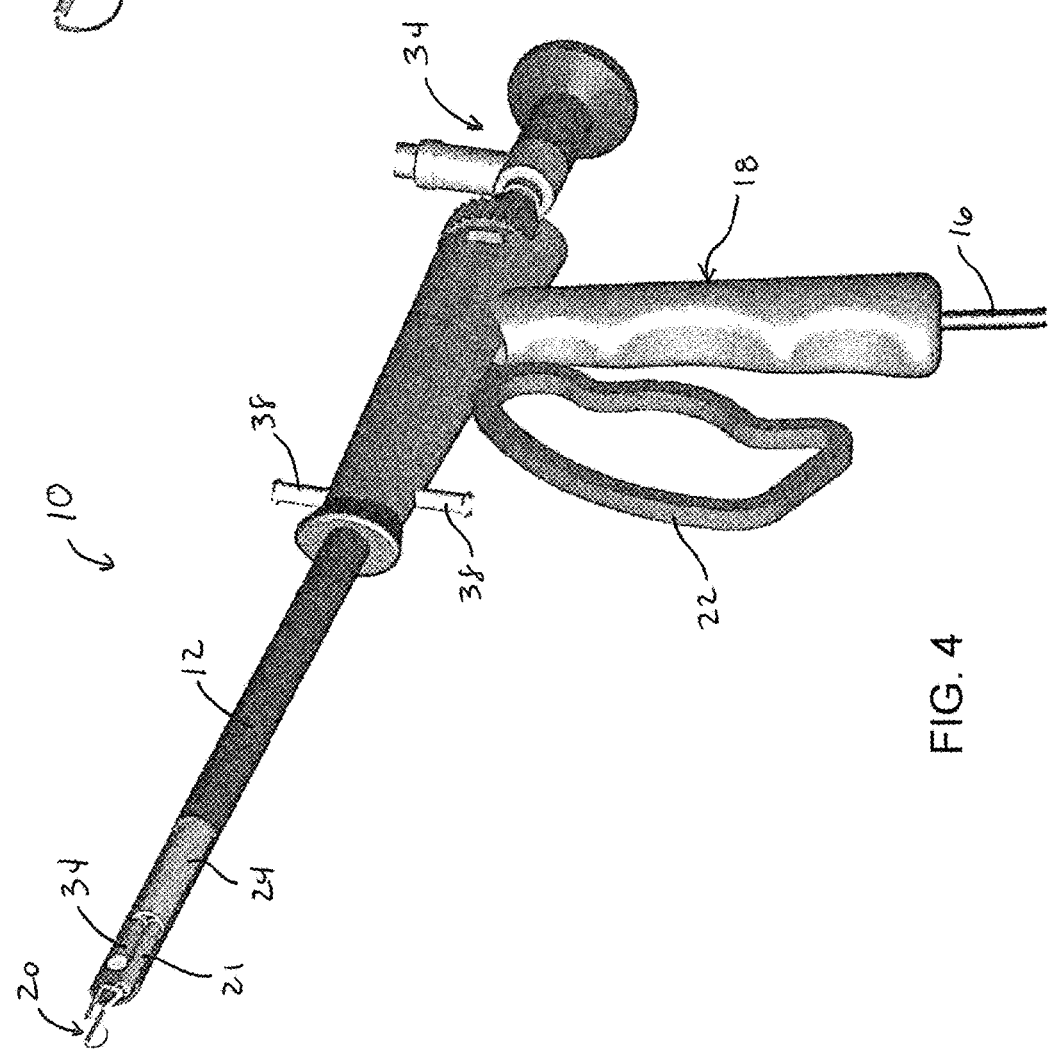
FIG. 4 is a perspective view of the probe of FIG. 1, showing a partial cutaway of the distal end of the sheath to reveal a core member of the probe and components disposed therein.

FIGS. 1 through 6 depict an electrosurgical probe 10 in accordance with a nonlimiting embodiment of the present invention. The drawings depict the probe 10 as a resectoscope, though other electrosurgical probes capable of use in a wide variety of procedures are also within the scope of the invention. The probe 10 is represented as including a sheath 12 through which conductors can be routed to one or more electrodes disposed at a distal end 14 of the sheath 12. The conductors carry a current, preferably an RF current, generated by an electrosurgical generator (not shown) that is connected to the probe 10 via a power cord 16 extending from a working element 18 of the probe 10. The probe 10 can be a monopolar or bipolar RF electrosurgical probe. FIGS. 1 through 5 depict a single electrode 20 configured as a cutting loop (wire), though other electrode configurations are possible and within the scope of this invention, for example, such well-known types as ball tip, disk, roller tip, barrel, cone, point, knife, flat band, coagulating, and punctate electrodes. As a cutting loop, the electrode 20 is represented as electrically connected to one or more insulated conductors 21 to define an active (+) pole of the RF circuit.

Figure 6:
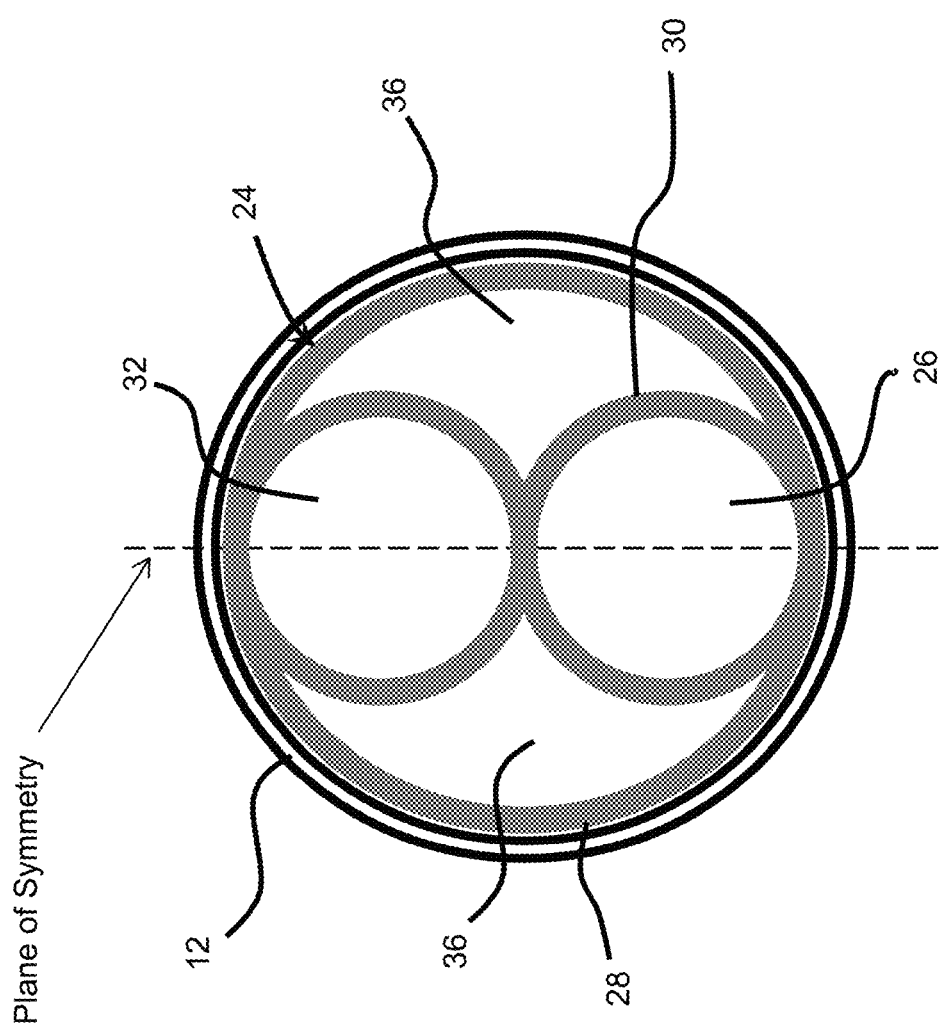
FIG. 6 represents an end view of the sheath and core member of the probe of FIGS. 1 through 5.

The electrode 20 and its conductors 21 are preferably capable of reciprocal movement within the sheath 12, as evidenced by the retracted and extended positions of the electrode 20 depicted in FIGS. 1 and 2, respectively. Movement of the electrode 20 and conductors 21 relative to the sheath 12 can be effected through the operation of an actuation lever 22 of the working element 18. The electrode 20 and its conductors 21 are disposed in an internal longitudinal channel 26 defined within a core member 24 that is coaxially disposed within an internal passage 25 defined by the sheath 12, such that the core member 24 is completely surrounded by the sheath 12. The electrode 20 and its conductors 21 may be reciprocably disposed in the internal channel 26, or the core member 24 may be reciprocably disposed within the passage 25 of the sheath 12. As evident from FIGS. 4 through 6, the core member 24 has a circular-shaped outer circumference defined by a tubular outer wall 28 of the member 24, and an internal web 30 that defines the internal channel 26 as well as a second internal longitudinal channel 32 in which a telescope 34 is represented as being received to allow direct vision during placement and use of the probe 10. The internal channels 26 and 32 preferably have circular cross-sections and the core member 24 is represented as having a plane of symmetry through the channels 26 and 32, with the result that the channels 26 and 32 are between two internal longitudinal channels 36 that are defined by the remainder of the circular interior cross-section of the core member 24 surrounded by the outer wall 28, as seen in FIG. 6. As a result of the circular cross-sectional shapes of the outer wall 28 and channels 26 and 32 and the symmetrical shape of the core member 24, the channels 36 are substantially identical mirror-images of each other and have fan-shaped cross-sections. Either or both of the channels 36 can serve as an irrigation tube that enables an irrigation fluid to be delivered to the electrode 20, for example, to perform immersion cooling of the electrode 20. Alternatively, a separate tube could be located within either or both channels 36 through which an irrigation fluid could flow through the sheath 12. In either case, at least one of the channels 36 is adapted to be fluidically coupled to a fluid source, for example, via one or more irrigation ports 38 located on the working element 18. As a result of the channels 36 being disposed on opposite sides of the channel 26 containing the electrode 20, the channels 36 are able to direct irrigation fluid to opposite sides of the electrode 20, thereby enveloping the electrode 20 and promoting the desired effect of the irrigation fluid in close proximity to the electrode 20.

Whereas the telescope 34, RF generator, and other such components including light sources are capital equipment of the probe 10, a preferred aspect of the invention is that the sheath 12, working element 18, electrode 20, and core member 24 are disposable and intended to be discarded after a single use, and therefore do not require sterilization after use and are not required to be formed of a stainless steel or other durable metallic material that would enable these components to be sterilized and reused. For example, the sheath 12, working element 18, and core member 24 can be formed of polymeric materials, including but not limited to plastics of the types commonly used for disposable surgical components, for example, plastics manufactured in an FDA/ISO Certified Facility with FDA marketing clearance. As such, the term "disposable" is used and defined herein to mean an article that is not adapted to be cleaned, sterilized, and reused for a medical procedure performed on a patient, and therefore is required to be marked with the ⓼ ISO symbol as a disposable (i.e., single-use) device. If the sheath 12, working element 18, and core member 24 are formed of electrically dielectric polymeric materials, the conductors 21 of the electrode 20 may be routed through the sheath 12 without requiring electrical insulation. Optionally, the distal end 14 of the sheath 12, including that portion of the sheath 12 that protrudes over the opening of the sheath passage 25, may be formed of or coated with a material that offers a greater degree of erosion and heat resistance to the high RF current levels, a notable but nonlimiting example of which is a phenol-formaldehyde resin such as Bakelite. Though also intended to be disposable, preferred materials for the electrode 20 include tungsten and stainless steels, though other materials could be used.

To facilitate use of the probe 10, the sheath 12, working element 18, electrode 20, core member 24, and telescope 34 of the probe 10 are preferably separable, allowing the electrode 20 to be removed from the core member 24, allowing the core member 24 to be removed from the sheath 12, and allowing the sheath 12, core member 24 and telescope 34 to be separated from the working element 18. The conductors 21 for the electrode 20 can be permanently fixed within the core member 24 or within the working element 18, in which case the electrode 20 can preferably be electrically coupled and decoupled from the conductors 21 and/or the conductors 21 can preferably be electrically coupled and decoupled from the working element 18 with suitable quick-connect features.

In view of the above, with the possible exception of the telescope 34, all of the components of the probe 10 depicted in FIGS. 1 through 6 are intended to be disposable. Due to being disposable, the electrosurgical probe 10 can reduce if not eliminate the handling, sterilization, packaging, and testing of and risk of damage to individual reusable components of probes that are currently used in electrosurgical procedures at surgery centers and hospitals. The risk of injury and/or contamination to the personnel involved with this process can be virtually eliminated with the disposable electrosurgical probe 10. The electrosurgical probe 10 is not required to be re-sterilized after use, as is conventional with reusable electrosurgical probes, though it should be understood that each individual disposable electrosurgical probe 10 would be pre-sterilized prior to use to ensure safety. Maintenance, wear due to use, and cross-contamination are also avoided with the disposable electrosurgical probe 10. Furthermore, it is foreseeable that the disposable electrosurgical probe 10 may be readily adapted or adaptable to particular brands of generators and telescopes.

The electrosurgical probe 10 and its components shown in FIGS. 1 through 6, as well as other optional components and materials, can be packaged together to form what will be referred to as a "disposable electrosurgical kit" or simply a "kit." The convenience and ability to access one kit with all the necessary components in a ready-to-use sterile package reduce the time and frustration that can be encountered when attempting to ensure that an electrosurgical probe and its components are available and ready to perform an electrosurgical procedure. Other major advantages include the ability to customize an individual kit, for example, to provide electrodes of various configurations within a single kit. In addition, the kit can offer different types of tubing connections to provide secure attachment to a scope, including but not limited to a stopcock, tubing with stopcock, and/or a luer connector.

The disposable electrosurgical kit has the ability to save money, reduce procedure time, reduce the risk of hospital-acquired infections by patients, and reduce the risk of injury or infections to hospital personnel and physicians. The functionality of the disposable electrosurgical probe 10 and kit relative to conventional reusable electrosurgical probes is not affected by its disposable nature, as RF generators, light sources, and telescopes usable with the probe 10 can be the same as those commercially available and commonly used at surgery centers and hospitals. As such, physicians may maintain the power and optical equipment they are familiar with.

While the invention has been described in terms of specific embodiments, it is apparent that other forms could be adopted by one skilled in the art. For example, the physical configuration of the disposable electrosurgical probe 10 could differ from that shown, a disposable telescope could be used, and materials and processes other than those noted could be used. Therefore, the scope of the invention is to be limited only by the following claims.

The invention claimed is:
1. An electrosurgical probe comprising:
a disposable working element comprising a core member having a plurality of internal longitudinal channels;
a disposable elongate sheath secured to the working element, the sheath having a sheath passage in which the core member is disposed such that the sheath surrounds the core member, the sheath passage having an opening at a distal end of the sheath;

a conductor disposed in a first of the internal longitudinal channels of the core member, the conductor being reciprocable within the sheath and permanently fixed within the core member;

an active electrode electrically coupled to the conductor and configured to be electrically decoupled from the conductor, the active electrode being adapted to receive a radio frequency current from and return the radio frequency to the conductor when electrically coupled to the conductor, the active electrode extending from the opening at the distal end of the sheath and being configured to perform cutting, coagulation, or ablation of tissue when the radio frequency current flows to the active electrode; and an irrigation tube defined by a second of the internal longitudinal channels of the core member and configured to couple with an irrigation fluid source and provide an irrigation fluid to the active electrode from the irrigation fluid source;

wherein the working element comprises means for reciprocating the active electrode relative to the sheath; and wherein the sheath and the working element, including the core member and the reciprocating means of the working element, are each single-use components formed of disposable materials and the electrosurgical probe is marked as disposable and not for reuse in a medical procedure performed on more than one patient.

2. The electrosurgical probe of claim 1, further comprising a telescope disposed in a third of the internal longitudinal channels of the core member and separable from the sheath, the working element, and the core member.

3. The electrosurgical probe of claim 2, wherein the telescope is adapted to be separated from the sheath, the working element, and the core member and then cleaned, sterilized, and reused for a medical procedure performed on more than one patient.

4. The electrosurgical probe of claim 1, wherein the core member comprises a tubular outer wall and an internal web within and integral with the tubular outer wall that divides a cavity within the tubular outer wall into the plurality of internal longitudinal channels.

5. The electrosurgical probe of claim 4, wherein the irrigation tube defined by the second internal longitudinal channel of the core member is a first irrigation tube, the core member comprises a third of the internal longitudinal channels that defines a second irrigation tube, and the first irrigation tube is a mirror-image of the second irrigation tube relative to a plane of symmetry through the first internal longitudinal channel.

6. The electrosurgical probe of claim 5, wherein the first irrigation tube defined by the second internal longitudinal channel and the second irrigation tube defined by the third internal longitudinal channel each have an arcuate convex outer wall defined by the tubular outer wall of the core member and two concave internal walls defined by the internal web of the core member.

7. The electrosurgical probe of claim 1, wherein the sheath, the working element, and the active electrode are configured to be separable and removable from each other.

8. The electrosurgical probe of claim 1, wherein the core member is configured to be removable from the sheath.

9. The electrosurgical probe of claim 1, wherein the sheath is configured to be separable from the working element.

10. The electrosurgical probe of claim 1, wherein the sheath and the working element, including the core member and the reciprocating means of the working element, are each formed of an electrically dielectric polymeric material.

11. The electrosurgical probe of claim 1, wherein the conductor is disposed within the first internal longitudinal channel of the core member without electrical insulation therebetween.

12. The electrosurgical probe of claim 1, wherein a portion of the sheath protrudes over the opening of the sheath passage, the portion of the sheath being formed of or coated with a material having a greater degree of erosion and heat resistance to the radio frequency current than the disposable material that forms a remainder of the sheath.

13. The electrosurgical probe of claim 12, wherein the material of the portion of the sheath is a phenol-formaldehyde resin.

14. The electrosurgical probe of claim 1, further comprising at least a second active electrode configured to be electrically coupled and decoupled from the conductor.

15. The electrosurgical probe of claim 1, wherein the electrosurgical probe is a urological or hysteroscopic electrosurgical probe.

16. A method of using the electrosurgical probe of claim 1 as a single-use device to perform a medical procedure, the method comprising:

placing the active electrode of the electrosurgical probe within a patient;

performing an electrosurgical procedure on the patient using the electrosurgical probe; and then discarding the working element, the core member thereof, the sheath, and the active electrode after performing the electrosurgical procedure, wherein the placing and performing steps are the first and only medical procedure in which the working element, the sheath, and the active electrode are used.

17. A medical procedure comprising:

placing within a patient an active electrode of an electrosurgical probe, the electrosurgical probe comprising a working element comprising a core member, an elongate sheath that is secured to the working element, surrounds the core member, and has an opening from which the active electrode protrudes, and a conductor within the sheath and permanently fixed within the core member, wherein the active electrode is electrically coupled to the conductor and wherein the sheath and the working element are each single-use components formed of disposable materials and the electrosurgical probe is marked as disposable and not for reuse in a medical procedure performed on more than one patient;

performing a single electrosurgical procedure on the patient using the active electrode of the electrosurgical probe;

electrically decoupling the active electrode from the conductor; and then discarding the working element, the sheath, and the active electrode after performing the electrosurgical procedure, wherein the placing and performing steps are the first and only medical procedure in which the working element, the sheath, and the active electrode are used.

18. The medical procedure of claim 17, wherein the electrosurgical procedure is a urological or hysteroscopic procedure.

* * * * *